(12) United States Patent
Hamprecht

(10) Patent No.: US 6,191,265 B1
(45) Date of Patent: Feb. 20, 2001

(54) THERMOMIGRATIONFAST AZO DYES

(75) Inventor: Rainer Hamprecht, Odenthal (DE)

(73) Assignee: DyStar Textilfarben GmbH & Co. Deutschland KG (DE)

( * ) Notice: Under 35 U.S.C. 154(b), the term of this patent shall be extended for 0 days.

(21) Appl. No.: 09/461,477

(22) Filed: Dec. 14, 1999

(30) Foreign Application Priority Data

Dec. 21, 1998 (DE) .............................. 198 58 997

(51) Int. Cl.$^7$ .............................. C09B 29/08; D06P 1/18; D06P 5/24; B41M 5/38

(52) U.S. Cl. .................. 534/730; 534/731; 534/753; 534/788; 534/853; 558/56; 8/466; 8/471; 8/680; 8/693; 503/227; 428/195; 428/913; 428/914

(58) Field of Search ..................... 534/730, 731, 534/853, 753, 788; 558/56; 8/466, 680, 693, 471; 503/227; 428/195, 913, 914

(56) References Cited

U.S. PATENT DOCUMENTS

| | | | |
|---|---|---|---|
| 4,249,275 | 2/1981 | Hugl et al. | 8/532 |
| 4,619,993 | 10/1986 | Baumann | 534/735 |
| 5,194,598 | 3/1993 | Hamprecht | 534/852 |

FOREIGN PATENT DOCUMENTS

| | | |
|---|---|---|
| 15 44 563 | 1/1985 | (DE) . |
| 217 232 | 1/1985 | (DE) . |
| 29 16 861 | 1/1985 | (DE) . |
| 313 918 | 1/1985 | (EP) . |
| 33 00 914 | 1/1985 | (DE) . |
| 1 125 683 | 8/1968 | (GB) . |
| 1 479 085 | 7/1977 | (GB) . |
| 2 012 799 | 8/1979 | (GB) . |
| 2 034 736 | 6/1980 | (GB) . |
| 47-25487 | * 10/1972 | (JP) . |
| 47-25488 | * 10/1972 | (JP) . |

* cited by examiner

Primary Examiner—Fiona T. Powers
(74) Attorney, Agent, or Firm—Connolly Bove Lodge & Hutz LLP

(57) ABSTRACT

Azo dyes of the formula

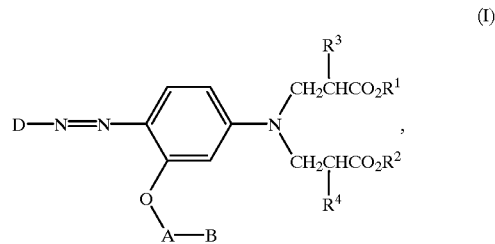

wherein the substituents are each as defined in the description, are useful for dyeing and printing synthetic textile materials.

14 Claims, No Drawings

THERMOMIGRATIONFAST AZO DYES

This invention relates to azo dyes of the formula

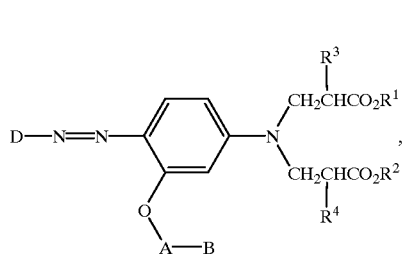

(I)

wherein

D is aryl or hetaryl other than 2,4-dinitro-6-ethanesulphonylphenyl,

A is —CO— or —SO—,

B is optionally substituted $C_1$–$C_4$-alkyl, $R^1$ and $R^2$ are independently optionally OH— or $C_1$–$C_4$-alkoxy-substituted $C_1$–$C_4$-alkyl, and $R^3$ and $R^4$ are independently H or $CH_3$, with the proviso that A is $SO_2$ when D is a 6-nitrobenzothiazolyl radical.

Useful substituents for the optionally substituted $C_1$–$C_4$-alkyl B are Cl, $C_1$–$C_4$-alkoxy, $C_1$–$C_4$-acyloxy, $CO_2$–$C_1$–$C_4$-alkyl.

Suitable aryls D are substituted benzene derivatives of the formula (II)

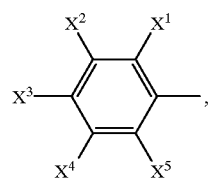

(II)

wherein $X^1$ and $X^5$ are independently H, F, Cl, Br, —$NO_2$, —CN, —$SO_2$—B, —$CO_2$—B, —OH, —CHO or —CO—B, $X^2$ and $X^4$ are independently H, Cl, Br, $NO_2$ or B, $X^3$ is H, Cl, Br, —$NO_2$, —CN, —$SO_2$—B, —$CO_2$—B, —CH=O or B, and B is as defined above.

Preferred hetaryls D are thiazoles (IIIa), isothiazoles (IIIb), thiophenes (IIIc), thiadiazoles (IIId), benzothiazoles (IIIe) and benzisothiazoles (IIIf) of the following formulae:

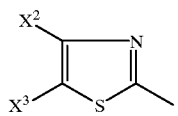

(IIIa)

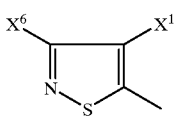

(IIIb)

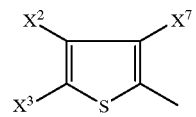

(IIIc)

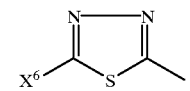

(IIId)

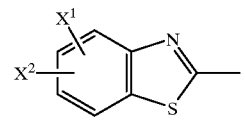

(IIIe)

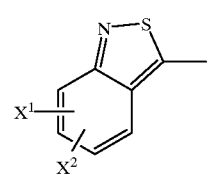

(IIIf)

wherein $X^1$ to $X^5$ are each as defined above, $X^6$ is H, B, Cl, Br, —SB or —$SO_2$B, $X^7$ is CN, —$CO_2$B or —CO—B, and B is as defined above.

Preference is given to dyes of the formula (I) wherein D is a radical of the formula

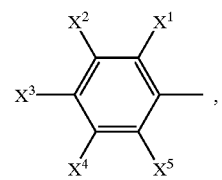

(II)

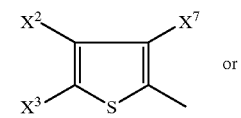

(IIIc)

or

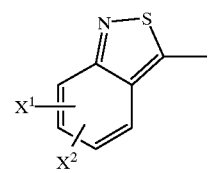

(IIIf)

wherein $X^1$ and $X^5$ are independently H, Cl, Br, CN, —$NO_2$, —$SO_2$—B or $CO_2$—B, $X^2$ and $X^4$ are independently H, B, Cl or Br, $X^3$ is H, B, Cl, Br, —$NO_2$, CN, —$CO_2$—B or —CH=O, $X^7$ is —CN, —$CO_2$—B, —CO—B, and B is as defined above.

Particular preference is given to dyes of the formula (I) wherein

D is a radical of the formula

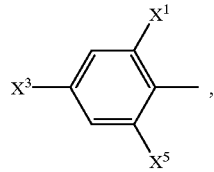
(V)

wherein $X^1$ is H, Cl, Br, CN or $NO_2$, $X^3$ is H, $CH_3$, Cl, Br or $NO_2$, $X^5$ is H, Cl, Br or CN, A is —SO—, B is optionally Cl-substituted $C_1$–$C_4$-alkyl, especially methyl, $R^1$ and $R^2$ are each $C_1$–$C_4$-alkyl, especially methyl, and $R^3$ and $R^4$ are each hydrogen.

The dyes (I) are prepared by generally customary methods. For example, diazo components of the formula

D—$NH_2$ (VI)

wherein

D is as defined above, are diazotized and coupled onto coupling components of the formula

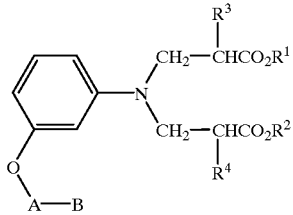
(VII)

wherein

A, B, $R^1$, $R^2$, $R^3$ and $R^4$ are each as defined above.

The diazotization is effected in the usual manner at −20 to 20° C. with the aid of alkali metal nitrites, nitrosylsulphuric acid or esters of nitrous acid in mineral acids (HCl, $H_2SO_4$, $H_3PO_4$) or lower fatty acids (acetic and/or propionic acid). The coupling is likewise carried out by customary methods, preferably by adding the aqueous solution or dispersion or aqueous/alcoholic solution to the diazonium salt solution and, if appropriate, adjusting the reaction mixture to pH 5–7 by addition of alkali.

A preferred process for preparing inventive 2,6-dicyanoazo dyes of the formula

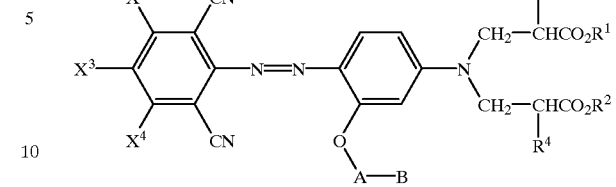
(VIII)

wherein $R^1$ to $R^4$, A, B and $X^2$ to $X^4$ are each as defined above, is characterized in that conventionally prepared azo compounds of the formula

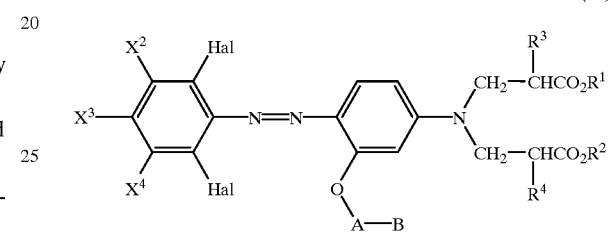
(IX)

wherein $R^1$ to $R^4$, A, B and $X^2$ to $X^4$ are each as defined above, and

Hal is halogen, preferably Cl or Br, have their halogen atoms exchanged for cyano groups.

This exchange reaction is likewise known per se and described for example in the following patent literature: DE-A 1 544 563=GB 1 125 683; DE-A 2 456 495=GB 1 479 085; DE-A 2 759 103=GB 2 012 799; DE-A 2 846 439=GB 2 034 736; DD 2 17 232 (especially the references cited therein).

Thereafter, the o,o'-dihaloazo compound is reacted with metal cyanides or cyanide ion donor compounds in a polar organic solvent or water at temperatures of 50 to 150° C. until the halogen atoms are virtually completely replaced, which is readily monitorable by reference to thin layer chromatograms.

Suitable cyanides are in particular CuCN and $Zn(CN)_2$ and complex cyanides of the formula $Me^{\oplus}{}_n(CuCN)_{n+1}$ (Me=Na, K; n=1–3). Suitable cyanide ion former systems are for example fornaldroxime, cyanohydrins, nitroalkanes or formamide.

Preferred organic solvents are polar aprotic compounds such as, for example, DMF, DMSO, pyridine, N-methylpyrrolidone, chlorobenzene, dichlorobenzenes, etc.

A particularly suitable and preferred way of carrying out the halogen/cyano exchange is by means of a mixture of copper(I) cyanide and zinc cyanide.

Whereas the diazo components are generally known, only the precursors are known of the coupling components, cf. for example EP 313 918 or U.S. Pat. No. 5,194,598.

However, these compounds are readily obtained in a manner known per se, for example by reacting compounds of the formula

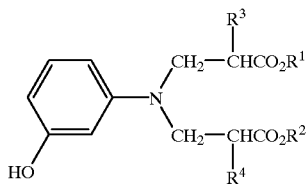 (X)

wherein
R¹ to R⁴ are each as defined above,
with
a) acid anhydrides, for example of the formula

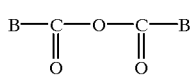

wherein
B is as defined above, or
b) acid chlorides of the formula

wherein
B and A are each as defined above.

The coupling components of the formula (VII) wherein B, R¹, R², R³ and R⁴ are each as defined under the formula (I) and A is $SO_2$ are new and likewise form part of the subject-matter of the present invention.

These acylations are preferably carried out in organic, preferably anhydrous, solvents. Water/organic solvent two-phase systems are also suitable.

Examples of suitable solvents are apolar organic solvents such as chlorinated hydrocarbons, for example methylene chloride, carbon tetrachloride, aromatic solvents, for example toluene, xylenes, chlorobenzene, dichlorobenzene, nitrobenzene, but also polar solvents such as acetone, dimethylformamide, N-methylpyrrolidone, sulpholane, etc.

It may be advantageous to use organic or inorganic bases to scavenge the hydrogen chloride formed.

Examples of suitable bases are sodium hydroxide, potassium hydroxide, sodium carbonate, potassium carbonate, sodium bicarbonate, potassium bicarbonate, sodium hydrogenphosphate, sodium acetate and also amines such as, for example, trialkylamines, pyridine, dialkylaminopyridine, quinoline, dialkylanilines, etc.

The dyes of the invention, as is customary for disperse dyes, are virtually insoluble in water. They are particularly useful for dyeing and printing synthetic textile materials, especially textile materials composed of secondary cellulose acetate and cellulose triacetate, polyamide, for example polyhexamethyleneadipamide, and most suitably aromatic polyester, for example polyethylene terephthalate, by the dyeing and printing methods customary for these fibre varieties using aqueous or non-aqueous liquors or print pastes.

The dyes may lastly also be applied to synthetic textile materials by thermal transfer printing.

The dyes are further useful for thermal transfer printing on synthetic recording materials in optical recording processes, for example for printing polyester-coated paper.

The scarlet to blue dyeings on polyester obtained with the new dyes combine good all round fastnesses with high colour strength, bright hues and, in particular, excellent thermomigrationfastness.

Compared with the closest known dyes of JP-A 47 25 487, which have a 6-nitrobenzothiazole diazo component, and JP-A 4725488, which have a 2,4-dinitro-6-ethylsulphonylphenyl diazo component, the new dyes have superior fastness properties.

EXAMPLES

Example 1

Preparation of the dye of the formula

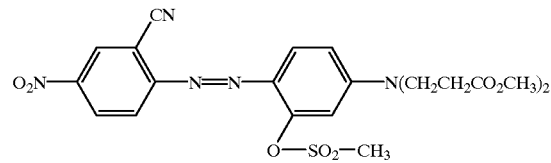

To a solution of 7.3 g of 2-cyano-4-nitroaniline in 30 ml of propionic acid and 60 ml of glacial acetic acid were added dropwise over 30 minutes at 0 to 5° C. 8.3 ml of a 42 per cent strength nitrosylsulphuric acid solution in sulphuric acid with stirring. The mixture was subsequently stirred at 0° C. for two hours.

The above diazotization mixture was gradually added at 0° C. to a solution of 16.4 g of β-alanine N-(3-methoxy-3-oxopropyl)-N-[3-[(methanesulphonyl)oxy]phenyl]-methyl ester and 2 g of amidosulphonic acid in 200 ml of methanol, ice-water being added to make up to a volume of 1500 ml. Overnight stirring was followed by suction filtration and washing until neutral. Yield: 19.9 g. The crude product was recrystallizable from DMF.

$\lambda_{max}$: 503 nm ($CH_2Cl_2$)

The dye dyes polyester in a bluish red having good fastnesses, especially very good thermomigrationfastness.

The coupling component needed is obtainable by reacting β-alanine N-(3-methoxy-3-oxopropyl)-N-[3-[oxy]phenyl]-methyl ester with methanesulphonyl chloride in toluene at 70° C. in the presence of triethylamine.

Analogous or similar methods provide the dyes of the formula

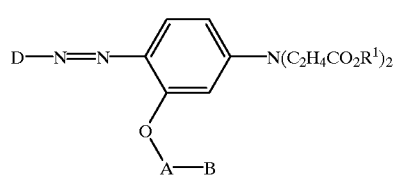

reported in the tables hereinbelow, dyes where A=$SO_2$ being described in Table 1 and dyes where A=CO in Table 2.

TABLE 1

| Ex. No. | D | B | R¹ | Hue on polyester | $\lambda_{max}$ nm (CH$_2$Cl$_2$) |
|---|---|---|---|---|---|
| 2 | 3-Cl, 4-CH₃, 5-NO₂ phenyl (O₂N-, Cl, CH₃ substituted) | CH₃ | CH₃ | yellowish scarlet | 472 |
| 3 | 2-CN, 4-NO₂, 6-CH₃ phenyl | CH₃ | C₂H₅ | bluish red | 507 |
| 4 | 2-CN, 4-NO₂, 6-CH₃ phenyl | C₂H₅ | CH₃ | bluish red | 502 |
| 5 | 2-CN, 4-NO₂, 6-CH₃ phenyl | C₄H₉ | CH₃ | bluish red | 503 |
| 6 | 2-CN, 4-NO₂, 6-CH₃ phenyl | CH₂Cl | CH₃ | red | 502 |
| 7 | 2,6-di-CN, 3-CH₃, 4-C₂H₅OCO phenyl | CH₃ | CH₃ | bluish red | 513 |
| 8 | 3,4-di-CH₃, 2-CN, 5-CN thiophene | CH₃ | CH₃ | reddish violet | 542 |
| 9 | 2-CN, 3-CH₃, 4-Br, 5-NO₂ phenyl | CH₂Cl | CH₃ | bordeaux | 511 |

TABLE 2

| Ex. No. | D | B | R¹ | Hue on polyester | $\lambda_{max}$ nm (CH$_2$Cl$_2$) |
|---|---|---|---|---|---|
| 10 | 2-CN, 4-NO₂, 6-CH₃ phenyl | CH₃ | CH₃ | bluish red | 509 |
| 11 | 2-CN, 3-CH₃, 5-NO₂ phenyl | C₂H₅ | CH₃ | bluish red | 510 |
| 12 | 2-CN, 4-NO₂, 6-CH₃ phenyl | C₃H₇ | CH₃ | bluish red | 510 |
| 13 | 2,6-di-CN, 3-CH₃, 5-Br phenyl | CH₃ | CH₃ | yellowish red | 496 |
| 14 | 2,6-di-CN, 3-CH₃, 5-C₆H₁₃O₂C phenyl | CH₃ | CH₃ | bluish red | 511 |
| 15 | 2-CN, 3-CH₃, 4-Br, 6-NO₂ phenyl | CH₃ | CH₃ | ruby | 514 |
| 16 | 5-NO₂ benzoisothiazolyl | CH₃ | CH₃ | reddish blue | 568 |
| 17 | 5-NO₂ benzoisothiazolyl (3-methyl) | C₂H₅ | CH₃ | reddish blue | 570 |
| 18 | 3,4-di-CH₃, 2-CN, 5-CN thiophene | CH₃ | CH₃ | reddish violet | 542 |

What is claimed is:

1. A dye of the formula:

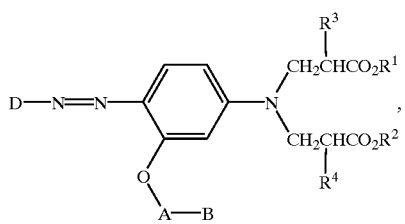
(I)

wherein

D is hetaryl or a radical of the formula (II)

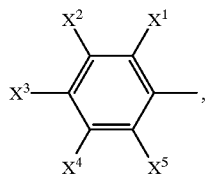
(II)

wherein $X^1$ and $X^5$ are independently is H, F, Cl, Br, —$NO_2$, —CN, —$CO_2$B, —OH, —CHO or —CO—B, $X^2$ and $X^4$ are independently H, Cl, Br, $NO_2$, or B, $X^3$ is H, Cl, Br, —$NO_2$, —CN, —$SO_2$B, —$CO_2$B, B or —CH=O, A is —CO— or —$SO_2$—, B is optionally substituted $C_1$–$C_4$-alkyl, $R^1$ and $R^2$ are independently optionally OH— or $C_1$–$C_4$-alkoxy-substituted $C_1$–$C_4$-alkyl, and $R^3$ and $R^4$ are independently H or $CH_3$, with the proviso that A is $SO_2$ when D is a 6-nitrobenzothiazolyl radical.

2. A dye of the formula:

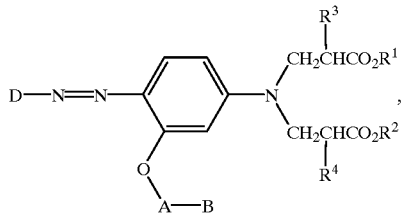
(I)

wherein

D is a radical of the formulae (IIIa) to (IIIf)

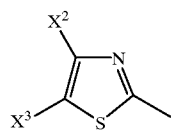
(IIIa)

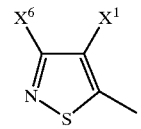
(IIIb)

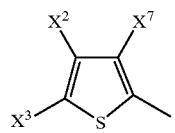
(IIIc)

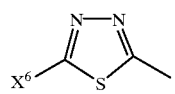
(IIId)

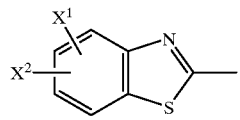
(IIIe)

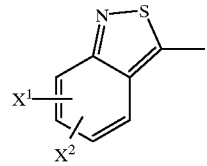
(IIIf)

wherein $X^1$ to $X^5$ are independently H, F, Cl, Br, —$NO_2$, —CN, —$SO_2$—B, —$CO_2$—B, —OH, —CHO or —CO—B, $X^6$ is H, B, Cl, Br, —SB or —$SO_2$B, $X^7$ is CN, —$CO_2$B or —CO—B, and B is optionally swbstituted $C_1$–$C_4$-alkyl.

3. The dye according to claim 1, wherein

D is a radical of the formula

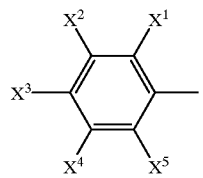
(II)

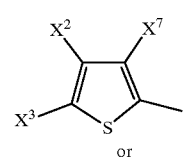
(IIIc)

or

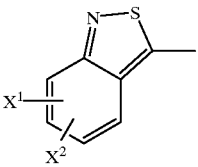
(IIIf)

wherein $X^1$ and $X^5$ are independently H, Cl, Br, CN, —$NO_2$, or $CO_2$—B, $X^2$ and $X^4$ are independently H, B, Cl or Br, $X^3$ is H, B, Cl, Br, —$NO_2$, CN, —$CO_2$—B or —CH=O, $X^7$ is —CN, —$CO_2$—B or —CO—B, and B is optionally substituted $C_1$–$C_4$-alkyl.

4. The dye according to claim 1, wherein
D is a radical of the formula

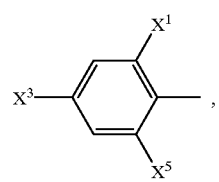
(V)

wherein $X^1$ is H, Cl, Br, CN or $NO_2$, $X^3$ is H, $CH_3$, Cl, Br or $NO_2$, $X^5$ is H, Cl, Br or CN, A is —$SO_2$—, B is optionally Cl-substituted $C_1$–$C_4$-alkyl, $R^1$ and $R^2$ are each $C_1$–$C_4$-alkyl, and $R^3$ and $R^4$ are each hydrogen.

5. A dye according to claim 1 of the formula

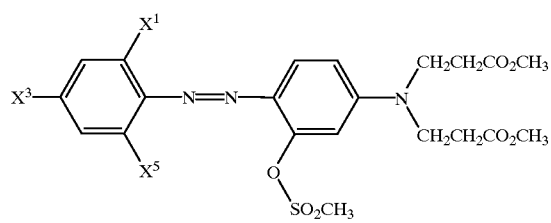

wherein $X^1$ is H, Cl, Br, CN or $NO_2$, $X^3$ is H, $CH_3$, Cl, Br or $NO_2$, and $X^5$ is H, Cl, Br or CN.

6. Process for preparing the dye according to claim 1, which comprises diazotizing diazo components of the formula

D—$NH_2$ (VI)

wherein
D is as defined in claim 1,
and coupling onto coupling components of the formula

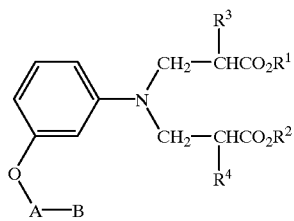
(VII)

wherein
A, B, $R^1$, $R^2$, $R^3$ and $R^4$ are each as defined in claim 1.

7. A compound of the formula

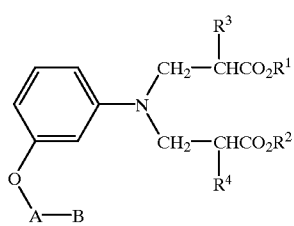
(VII)

wherein

B is optionally substituted $C_1$–$C_1$-alkyl, $R^1$ and $R^2$ are independently optionally OH— or $C_1$–$C_4$-alkoxy-substituted $C_1$–$C_4$ alkyl, $R^3$ and $R^4$ are independently H or $CH_3$, and A is $SO_2$.

8. The dye as claimed in claim 4, wherein B is optionally Cl-substituted methyl and $R^1$ and $R^2$ are methyl.

9. A dye of the formula:

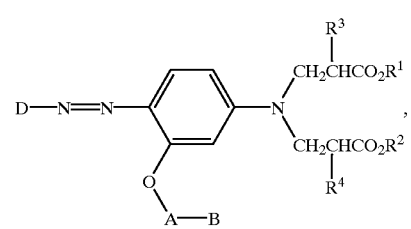
(I)

wherein
D is hetaryl or a radical of the formula (II)

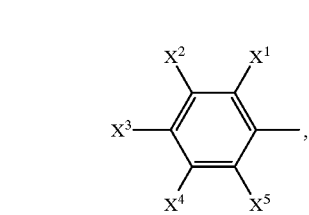
(II)

wherein $X^1$ and $X^5$ are independently is H, F, Cl, Br, —$NO_2$, —CN, —$CO_2$B, —OH, —CHO or —CO—B, $X^2$ and $X^4$ are independently H, Cl, Br, $NO_2$ or B,
$X^3$ is H, Cl, Br, $-NO_2$, $-CN$, $-CO_2B$, B or $-CH=O$,
A is $-CO-$ or $-SO_2-$,
B is optionally substituted $C_1-C_4$-alkyl,
$R^1$ and $R^2$ are independently optionally OH— or $C_1-C_4$-alkoxy-substituted $C_1-C_4$-alkyl, and
$R^3$ and $R^4$ are independently H or $CH_3$,
with the proviso that A is $SO_2$ when D is a 6-nitrobenzothiazolyl radical.

10. A process for dyeing or printing synthetic textile materials which comprises applying the dyes according to claim 1 to said material.

11. The process according to claim 10, wherein said material is secondary cellulose acetate, cellulose triacetate, polyamide or aromatic polyester.

12. A process for producing an optical recording material which comprises thermal transfer printing of the dye according to claim 1 on a synthetic recording material.

13. A process for printing on synthetic textile materials which comprises thermal transfer printing of the dye according to claim 1 on said synthetic textile material.

14. The process as claimed in claim 6, wherein said diazotizing is carried out at −20 to 20° C. with the aid of an alkali metal nitrite, nitrosylsulphuric acid or an ester of nitrous acid in mineral acid or lower fatty acid.

* * * * *